(12) United States Patent
Michaud et al.

(10) Patent No.: US 9,827,277 B2
(45) Date of Patent: Nov. 28, 2017

(54) SULPHATED POLYSACCHARIDE COMPOSITION

(71) Applicants: UNIVERSITÉ BLAISE PASCAL—CLERMONT II, Clermont-ferrand (FR); CENTRE NATIONAL DE LA RECHERCHE SCIENTIFIQUE (C.N.R.S), Paris (FR)

(72) Inventors: Philippe Michaud, Billom (FR); Celine Laroche, Crevant-Laveine (FR); Aurore Villay, Auzat la Combelle (FR); Michael Roussel, Clermont Ferrand (FR); Marie Diogon, Clermont Ferrand (FR); Hicham El Alaoui, Clermont Ferrand (FR); Frederic Delbac, Aubiere (FR)

(73) Assignees: UNIVERSITE BLAISE PASCAL—CLERMONT II, Clermont-Ferrand (FR); CENTRE NATIONAL DE LA RECHERCHE SCIENTIFIQUE (C.N.R.S), Paris (FR)

(*) Notice: Subject to any disclaimer, the term of this patent is extended or adjusted under 35 U.S.C. 154(b) by 0 days.

(21) Appl. No.: 14/442,884

(22) PCT Filed: Nov. 15, 2013

(86) PCT No.: PCT/EP2013/073995
§ 371 (c)(1),
(2) Date: May 14, 2015

(87) PCT Pub. No.: WO2014/076261
PCT Pub. Date: May 22, 2014

(65) Prior Publication Data
US 2015/0328253 A1   Nov. 19, 2015

(30) Foreign Application Priority Data
Nov. 16, 2012   (FR) ..................... 12 60941

(51) Int. Cl.
| A61K 36/02 | (2006.01) |
| A61K 31/737 | (2006.01) |
| A61K 35/748 | (2015.01) |
| A61K 36/05 | (2006.01) |
| A61K 36/03 | (2006.01) |
| A61K 36/04 | (2006.01) |
| A23K 20/147 | (2016.01) |
| A23K 20/163 | (2016.01) |
| A23K 50/90 | (2016.01) |
| A23L 33/105 | (2016.01) |

(52) U.S. Cl.
CPC .......... *A61K 35/748* (2013.01); *A23K 20/147* (2016.05); *A23K 20/163* (2016.05); *A23K 50/90* (2016.05); *A23L 33/105* (2016.08); *A61K 31/737* (2013.01); *A61K 36/03* (2013.01); *A61K 36/04* (2013.01); *A61K 36/05* (2013.01); *A23V 2002/00* (2013.01)

(58) Field of Classification Search
None
See application file for complete search history.

(56) References Cited

U.S. PATENT DOCUMENTS

| 2003/0181416 A1 | 9/2003 | Comper |
| 2011/0172156 A1 | 7/2011 | Dockal et al. |

FOREIGN PATENT DOCUMENTS

| EP | 0676206 A1 | 10/1995 |
| JP | 11-080003 A | 3/1999 |
| JP | H11 80003 A | 3/1999 |
| JP | 2000-336035 A | 12/2000 |
| JP | 2004-307346 A | 11/2004 |
| JP | 2006-502129 A | 1/2006 |
| JP | 2008-169181 A | 7/2008 |
| PT | 103 983 A | 8/2009 |
| WO | 9508334 A1 | 3/1995 |
| WO | 02/02189 A2 | 1/2002 |
| WO | 0202189 A2 | 1/2002 |
| WO | 02092114 A1 | 11/2002 |
| WO | 2009144711 A1 | 12/2009 |

OTHER PUBLICATIONS

Hayman et al (Infection and Immunity (2005), 73(2), 841-848).*
Jun-Hu Chen et al.: "Growth-inhibitory effect of a fucoidan from brown seaweed *Undaria pinnatifida* on Plasmodium parasites", Parasitology Research ; Founded as Zeitschrift Fur Parasitenkunde, Springer, Berlin, DE, vol. 104, No. 2, Sep. 13, 2008 (Sep. 13, 2008), pp. 245-250, XP019716049, ISSN: 1432-1955 pp. 247-248.
International Search Report, dated Jan. 23, 2014, from corresponding PCT application.
FR Search Report, dated May 2, 2013, from corresponding FR application.
Inagaki, S., et al., "Funoran-Containing Xylitol Gum and Tablets Inhibit Adherence of Oral Streptococci," J. Oral Biosci., vol. 53, No. 1, 2011, pp. 82-86.
Takano, R., et al., "Concurrence of Agaroid and Carrageenan Chains in Funoran from the Red Seaweed *Gloiopeltis furcata* Post. et Ruprecht (Cryptonemiales, Rhodophyta)," Carbohydrate Polyers, vol. 35, 1998, pp. 81-97.
Tuvikene, R., et al., "Funorans from *Gloiopeltis* Species. Part 1. Extraction and Structural Characteristics," Food Hydrocolloids, vol. 43, 2015, pp. 481-492.

* cited by examiner

*Primary Examiner* — Jennifer Graser
(74) *Attorney, Agent, or Firm* — Young & Thompson

(57) ABSTRACT

The invention concerns a composition made from at least one sulphated polysaccharide, in particular from an algae, and combined with at least one food ingredient. This composition can be used, in particular, in the field of food or in the treatment or prevention of an infection caused by microsporidia in humans or animals. It has useful properties as an antiparasitic agent in humans or animals; for the treatment or prevention of an infection caused by at least one microsporidia in humans or animals; in particular for the treatment or prevention of an infection caused in bees by the microsporidia *Nosema*, preferably *Nosema ceranae* or *Nosema apis*, or indeed for stimulating the immune defences of bees.

9 Claims, No Drawings

SULPHATED POLYSACCHARIDE COMPOSITION

The invention concerns a composition made from at least one sulphated polysaccharide, in particular derived from an algae, and combined with at least one food ingredient. This composition can be used, in particular, in the field of food or in the treatment or prevention of an infection caused by microsporidia in humans or animals.

It has useful properties as an antiparasitic agent in humans or animals; for the treatment or prevention of an infection caused by at least one microsporidium in humans or animals; in particular for the treatment or prevention of an infection caused in honey bees by the microsporidium *Nosema*, preferably *Nosema ceranae* or *Nosema apis*, or indeed for stimulating the immune defence system of the honey bee.

The invention also relates to the use of a sulphated polysaccharide as an antiparasitic agent in humans or animals in the treatment or prevention of at least one infection caused by at least one microsporidium in humans or animals, preferably by the microsporidium *Nosema* in honey bees.

The invention also relates to a method for treating or preventing an infection caused by at least one parasite in honey bees, comprising the administration of a composition according to the invention.

The invention also relates to a production method for producing honey in the presence of an infection caused by at least one parasite, comprising the administration to the honey bees of a composition according to the invention.

The invention also relates to a method for maintaining the pollination of plants by honey bees that have been infected by at least one parasite, comprising the administration of a composition according to the invention.

The invention also relates to a method for stimulating the immune defence system in honey bees, comprising the administration of a composition according to the invention.

Patent application US 2003/0181416 relates to a treatment method for treating microbial infection in mammals by making use of a sulphated polysaccharide.

Patent application JP 11080003 discloses an antiparasitic agent comprising a sulphated polysaccharide. JP 11080003 discloses in a generic manner fucoidan, sulphated rhamnan and carrageenan as polysaccharides.

Chen et al (Growth-inhibitory effect of a fucoidan from brown seaweed *Undaria pinnatifida* on *Plasmodium* parasites by Chen et al, published in September 2008) reports the results of a study pertaining to the antiparasitic effect on *Plasmodium falciparum* and *Plasmodium berghei* of three fractions of fucoidan derived from a brown alga, *Undaria pinnatifida*.

Patent application WO 02/02189 discloses the use of sulphated polysaccharides, in particular use of sulphated cellulose or sulphated dextran in anti-parasite treatments. These polysaccharides can be administered in the form of edible capsules or even in the form of a cream or gel.

Patent application US 2011/0172156 relates to the administration of sulphated polysaccharides in order to improve blood coagulation in a patient. These polysaccharides may be extracted from brown algae.

Paten application WO 2009/144711 discloses a nutritional or cosmetic composition comprising a metal and a sulphated polysaccharide derived from a red microalga. This composition is designed so as to make possible the administration of the metal that it contains. It is useful for nutritional or dermatological treatments and possesses antimicrobial properties.

Patent application PT 103983 discloses the use of sulphated polysaccharides as antiviral agents or antibacterial agents.

None of these documents relates to the prevention or treatment of an infection caused by a microsporidian pathogen in humans or animals.

Microsporidia, which are unicellular eukaryotic organisms related to fungi, are obligate intracellular parasites forming small sized spores that are able to persist in the environment for a long period extending over several months. Among the 1,300 species currently identified and listed, the majority parasitise arthropods and fish. Consequently, certain microsporidia are thus responsible for causing substantial economic losses in the aquaculture industry, in particular in the farming of salmon or shrimp. Several species are also responsible for causing various infections in mammals including in humans.

The *Nosema* disease (nosemosis), the causative agent of which is the microsporidium *Nosema* sp., is one of the diseases to be most frequently encountered in adult honey bees. This microsporidium invades the cells of the epithelium of the mid-gut of the insect and causes acute nosemosis characterised by traces of diarrhoea in the bee hives. It can reduce the life expectancy of the colonies. Recently, *Nosema ceranae* a microsporidian parasite common in the Asian honey bee (*Apis cerana*), was detected in colonies of European honey bees (*Apis mellifera*) that exhibited signs of weakening (Higes et al, *Nosema ceranae*, a new microsporidian parasite in honeybees in Europe. Journal of Invertebrate Pathology (2006), 92(2), 93-95; Cox-Foster et al, A metagenomic survey of microbes in honey bee colony collapse disorder. Science (2007) 318(5848), 283-287).

Given the ecological importance (biodiversity), and agricultural (crop yield) and economic impact (apiculture) that may be attributed to bees by virtue of their activities related to pollination and production of honey, the emergence of this microorganism has raised many concerns among the scientific and apicultural communities.

Moreover, the infection caused by *Nosema ceranae* brings about lowered immunity in the honey bee (AntUnez et al, Immune suppression in the honey bee (*Apis mellifera*) following infection by *Nosema ceranae* (Microsporidia). Environmental Microbiology (2009) 11 (9), 2284-2290), thereby making it more susceptible to other infections.

The main molecule used in treatment against *Nosema* disease (nosemosis) is fumagillin. However, this molecule has recently been banned in many European countries, including France.

Thus, the search for new molecules has become necessary in order to identify effective anti-parasite treatments, that cause no adverse effects on the parasitised host and do not generate hazardous residues in the food stuff derived from the hive.

The composition according to the invention makes it possible to provide a solution, in whole or part, to these problems or disadvantages of the state of the art.

Thus, the invention provides a composition comprising at least one sulphated polysaccharide and at least one food ingredient, for use thereof in the treatment or prevention of an infection caused by a microsporidian pathogen in humans or animals.

Thus, the food ingredient of the composition according to the invention corresponds to the portion of this composition that excludes the sulphated polysaccharide.

In an advantageous manner, the concentration by weight of sulphated polysaccharide in the composition according to the invention ranges from 0.01% to 2%, preferably from 0.1% to 1%.

In a preferable manner, the composition according to the invention comprises a sulphated polysaccharide which is of natural origin.

In an advantageous manner, the composition according to the invention may comprise at least one sulphated polysaccharide derived from a macroalga, a microalga or a *cyanobacterium* or even a mixture of sulphated polysaccharides derived from a macroalga, a microalga or a *cyanobacterium*.

By way of examples of sulphated polysaccharides of natural origin, the composition according to the invention preferentially comprises at least one sulphated polysaccharide derived from a macroalga, preferably selected from among the red macroalgae, the green macroalgae or the brown macroalgae.

In a highly preferred manner, the composition according to the invention comprises at least one sulphated polysaccharide derived from:
- a red macroalga, in particular selected from among the Rhodophyceae that produce agar, carrageenans, porphyrans, furonans, or complex sulphated galactans, preferably of the genera *Gracilaria, Halymenia, Gelidium, Pterocladia, Acanthopeltis, Campylaephora, Ceranium, Eucheuma, Chondrus, Porphyra, Laurencia, Furcellaria, Gloiopeltis* and *Iridea*;
- a green macroalga, in particular selected from the Chlorophyceae that produce polysaccharides like ulvan, preferably of the genus *Ulva*;
- a brown macroalga, in particular selected from the Pheophyceae that produce sulphated fucans, preferably of the genera *Fucus, Aschophyllum* or *Cladosiphon*.

The polysaccharides derived from red macroalgae are preferably constructed on the basis of a linear chain of 3-β-galactopyranose and 4-α-galactopyranose units alternating regularly. The β-galactose unit indeed still belongs to the D series, while the α-galactose unit has a D configuration in carrageenans and L configuration in agarocolloids (for example agar, porphyran, furonane). Furthermore, a part of the 4-α-galactopyranose residues may exist in the form of 3,6-anhydrogalactose. The 3,6-anhydrogalactose form is obtained by the elimination of the sulphate ester carried by the carbon 6 of the 4-linked α-galactose unit, under the action of galactose-6-sulfurylase during biosynthesis or by means of an alkaline treatment. Certain hydroxyl groups of these galactopyranose units may be sulphated, methylated, pyruvilated or indeed even substituted by a monosaccharide.

The sulphated galactans derived from red macroalgae may be represented by the formula (I) (Delattre et al, Galactans: An Overview of their Most Important Sourcing and Applications as Natural Polysaccharides. Brazilian Archives of Biology and Technology, 2011, 54: 1075-1092):

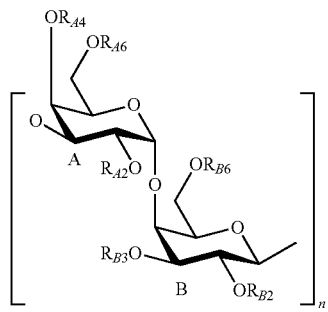

(I)

wherein:

$R_{A2}$ represents a hydrogen atom or $SO_3^-$;

$R_{A4}$ represents a hydrogen atom, $SO_3^-$ or pyruvic acid;

$R_{A6}$ represents a hydrogen atom, a methyl group, $SO_3^-$ or pyruvic acid;

$R_{B2}$ represents a hydrogen atom, a methyl group or $SO_3^-$;

$R_{B3}$ represents a hydrogen atom;

$R_{B6}$ represents a hydrogen atom or $SO_3^-$.

By way of examples of green macroalgae, mention may be made of the species belonging to the genera *Ulvella, Ulva, Caulerpa, Codium, Bryopsis*.

In general, three families of polysaccharides constitute the matrix polysaccharides of green algae.

The first one, the most prevalent, is constituted of a sulphated xylorhamnoglycuronane referred to as ulvan.

Polymers of this type are soluble in water and are distinguished from other polysaccharides extracted from algae by their high content of rhamnose (30% to 50%), glucuronic acid (10% to 20%), and sulphate (16% to 19%) (Lahaye et al, Structure and function properties of ulvan, a polysaccharide from green seaweeds; *Biomacromolecules* 8 (2007): 1765-1774; Lahaye, NMR spectroscopic characterization of oligosaccharides from two *Ulva rigida* ulvan samples (*Ulvales*, Chlorophyta) degraded by a lyase. *Carbohydrate Research* (2008) 314: 1-12). In the species *Ulva lactuca*, the main units are composed of type A ulvanobiuronate-3-sulphate comprising α-L-rhamnose-3-sulphate linked to the β-D-glucuronic acid by a (1,4) type bond and type B ulvanobiuronate-3-sulphate comprising α-L-rhamnose-3-sulphate linked to the α-L-iduronic acid by a (1,4) type bond (McKinnel et al, The acid polysaccharide from the green seaweed, *Ulva lactuca*. *Journal of Chemical Society* (1962) 398-399.; Quemener et al, Sugar determination in ulvans by a chemical-enzymatic method coupled to high performance anion exchange chromatography. *Journal of Applied Phycology* (1997) 9: 179-188). These units derived from ulvan have recently been augmented by the identification of ulvanobiose type structures (Robic, A, Rondeau-Mouro, C, Sassi, J F, Lerat, Y, Lahaye M (2009). Structure and interactions of ulvan in the cell wall of the marine green algae *Ulva rotundata* (*Ulvales*, Chlorophyceae). Carbohydrate Polymers 10: 210-216).

The ulvans may be represented by the formulas $A_{3S}$, $B_{3S}$, $U_{3S}$ and $U_{2'3S}$.

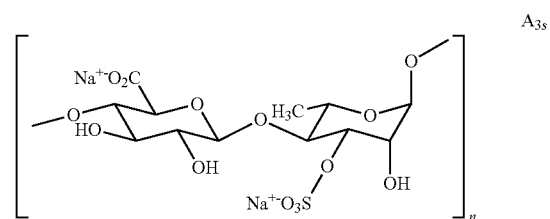

$A_{3s}$

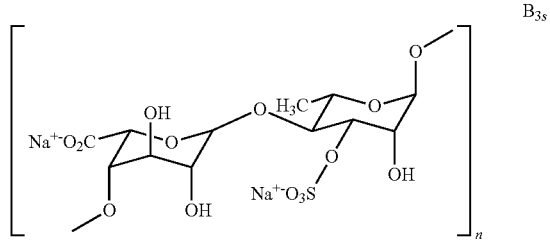

$B_{3s}$

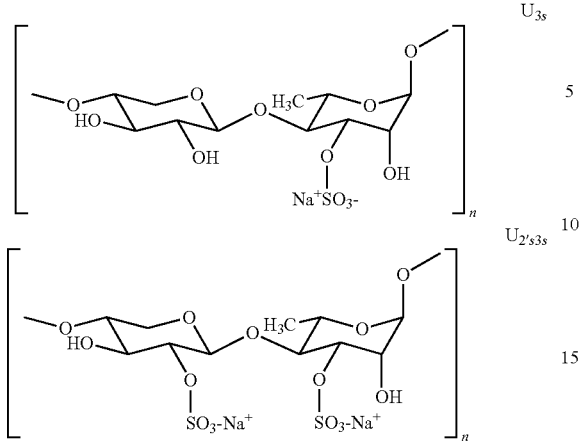

The second family of polysaccharides is composed of β-(1,4) linked D-xyloglucans and β-(1,4) linked D-glucuronans. These compounds may also be represented by the formulas $A_{3s}$, $B_{3s}$, $U_{3s}$ and $U_{2's3s}$.

The last family is represented by the amorphous "cellulose", containing xylose residues. In green algae of the order Cladophorales and Codiales, sulphated xylo-arabinogalactans may also be found. These are polymers that are composed of galactose, arabinose and xylose. They comprise about 17% of sulphate. There are really no repeating units, but rather, portions that include blocks of (1,4)-L-arabinose separated by D-galactose units. All of the D-xylose units and a part of the D-galactose units are in terminal position.

In an advantageous manner, the brown macroalgae is selected from the Phaeophyceae that produce sulphated fucans, preferably of the genera *Fucus, Aschophyllum* or *Cladosiphon*.

Fucans represent a class of sulphated polysaccharides containing predominantly L-fucose but also other saccharides with the suffix-ose such as galactose, mannose, xylose, and uronic acids (Melo et al, Isolation and characterization of soluble sulphated polysaccharide from the red seaweed *Gracilaria cornea. Carbohydrate Polymers* (2002) 49: 491-498) whose content is less than 10% (Berteau et al, Sulphated fucans, fresh perspectives: structures, functions, and biological properties of sulphated fucans and an overview of enzymes active toward this class of polysaccharide. *Glycobiology* (2003) 13 (6): 29-40).

Fucans extracted from algae of the order Fucales (*Fucus* sp, *Ascophyllum* sp) are highly branched polysaccharides (Berteau et al 2003; Patankar et al, 1993; Bilan et al, 2002, 2004, 2006) formed of one main chain composed of α-(1,3) or β-(1,4) linked L-fucose and variably substituted by 1 or 2 non-sugars (sulphate or acetate) on the C2, C3 or C4. These are homofucans (Chevolot et al, 1999, 2001; Bilan et al, 2002, 2004, 2006; Chizhov et al, 1999). These branches may be monosaccharide branches (Chizhov et al, A study of fucoidan from the brown seaweed *Chorda filum. Carbohydrate Research* (1999) 320:108-119), trisaccharide branches (Bilan et al, A highly regular fraction of a fucoidan from the brown seaweed *Fucus distichus. Carbohydrate Research* (2004), 339: 511-517) or tetrasaccharide branches (Bilan et al, Structure of a fucoidan from the brown seaweed *Fucus evanescens*. Ag. *Carbohydrate Research* (2002) 337: 719-730). Finally, the presence of xylose or galactose in small amounts could be detected but their location has not been determined (Bilan et al, 2002).

By way of another polysaccharide of natural origin, the composition according to the invention may also preferentially include a sulphated polysaccharide derived from a microalga, preferably selected from the red microalgae or cyanobacteria.

In an equally preferable manner, the composition according to the invention comprises at least one sulphated polysaccharide derived:
from a red microalga selected from the species belonging to the genus *Porphyridium* or the genus *Rhodella*.
from a *cyanobacterium* selected from the species belonging to the genus *Arthospira* such as *Arthospira platensis*.

The exopolysaccharides produced by marine red microalgae are mainly described in species belonging to the genera *Porphyridium* and *Rhodella*. These polysaccharides are heteropolymers that are variably sulphated and composed of neutral monosaccharides (xylose, glucose, galactose, mannose, arabinose, fucose), methylated monosaccharides (3-O-methyl xylose, 3-O and 4-O-methyl galactose), uronic acids (glucuronic acid) and methyl uronic acids (2-O-methylglucuronic acid). The polysaccharides of the different species present several types of glycoside bonds but have in common the presence of building blocks constituted of a disaccharide qualified as aldobiouronic acid (Arad et al, Red microalgal cell-wall polysaccharides: biotechnological aspects. Current opinion in Biotechnology (2010) 21: 358-364; Capek et al, The extracellular proteoglycan produced by *Rhodella grisea. International Journal of Biological macromolecules* (2008) 43, 390-393).

Cyanobacteria produce exopolysaccharides that have very complex structures and are characterised by the presence of uronic acids (glucuronic acid and galacturonic acid) and sulphate groups that serve to give the polysaccharide an anionic nature. They are further characterised by the presence of fairly high levels of acetate groups, peptide fractions and deoxy-monosaccharides. The majority of exopolysaccharides described in cyanobacteria are composed of at least six different monosaccharides and to date 12 monosaccharides have been identified in the exopolysaccharides (EPS) of cyanobacteria. Included among the hexoses are glucose, galactose, mannose and fructose. As for the pentoses, they are mainly represented by ribose, xylose and arabinose, while the deoxyoses identified are fucose, rhamnose and rhamnose methyl. In some cases, the presence of modified monosaccharides such as N-acetyl glucosamine, 2,3-O-methyl rhamnose, and 3-O-methyl glucose have been described. These various different monosaccharides are linked by a wide range of glycosidic bonds (Pereira et al, Complexity of cyanobacterial exopolysaccharides: composition, structures, inducing factors and putative genes involved in their biosynthesis and assembly. FEMS Microbiol. Rev. (2009) 33: 917-941).

In an equally advantageous manner, the composition according to the invention may comprise at least one sulphated polysaccharide obtained by chemical modification of a polysaccharide. The polysaccharide is then obtained after being modified by chemical means.

In a usual manner, the composition according to the invention comprises at least one sulphated polysaccharide of which the rate of sulphation on a weight basis is greater than or equal to 5%, preferably this rate ranges from 5% to 50%, preferably from 5% to 30%.

The composition according to the invention may comprise relatively large quantities of at least one sulphated polysaccharide.

Generally, the mass concentration of sulphated polysaccharide in the composition according to the invention ranges from 50 to 1,000 mg/mL, preferably from 100 to 1,000 μg/mL, advantageously from 100 to 200 μg/mL.

The composition according to the invention also comprises at least one food ingredient combined with at least one sulphated polysaccharide.

In an advantageous manner, the concentration by weight of the food ingredient in the composition according to the invention ranges from 98% to 99.99%.

In a general manner, the food ingredient of the composition according to the invention is an ingredient that can be used in a food composition meant for consumption by humans or animals. This food ingredient satisfies in particular all the conditions of safety and non-toxicity associated with such a use.

In a preferable manner, the composition according to the invention comprises at least one ingredient selected from a dietary protein agent, a sugar including sucrose, honey or one of the mixtures thereof.

In an advantageous manner, the composition according to the invention comprises a food ingredient of which the concentration by weight in the composition ranges from 98% to 99.99%, preferably from 99% to 99.9%.

In a preferred manner, the composition according to the invention comprises a food ingredient selected from among honey, saccharose (or sucrose), fructose, glucose, or maltose; preferably saccharose, honey or mixtures thereof.

The preferred mixtures of food ingredients for the composition according to the invention are selected from among the mixtures of proteins, honey and saccharose; mixtures of honey and saccharose. The composition according to the invention may comprise other combinations of food ingredients.

In the composition according to the invention the (sulphated polysaccharide/food ingredient) ratio by weight may vary relatively widely.

Generally, the (sulphated polysaccharide/food ingredient) ratio by weight in the composition according to the invention ranges from 0.0001 to 0.002, preferably from 0.0002 to 0.001, advantageously from 0.0002 to 0.0005.

The form of the composition may be defined in a rather broad sense. Thus, the composition according to the invention may in particular be in solid, paste or liquid form.

The invention also relates to a method of preparation, for preparing a composition according to the invention.

In a general sense, the method of preparation according to the invention includes the mixing of at least one sulphated polysaccharide and at least one food ingredient.

The method of preparation, for preparing the composition according to the invention may in particular include a step of sulphation of at least one polysaccharide.

This sulphation step may be applied to a polysaccharide that is slightly sulphated or non sulphated or to a sulphated polysaccharide in order to increase the rate of sulphation.

In a preferable manner, the method for preparing a composition according to the invention comprising a sulphated polysaccharide derived from a macroalga, includes:
 the preparation of solution of the sulphated polysaccharide from the macroalgae, possibly previously depigmented, by heating under reflux in water at a temperature ranging from 50° C. to 100° C.;
 the precipitation by at least one polar solvent or by means of dialysis of the sulphated polysaccharide;
 the drying of the sulphated polysaccharide.

The method of preparation according to the invention may comprise a prior step of depigmentation of the macroalga, in particular by means of at least one solvent which may be selected from acetone or chloroform.

In an advantageous manner, the precipitation may be carried out by making use of a polar solvent, for example ethanol or propanol.

Also in an advantageous manner, the drying may be brought about by lyophilisation (freeze drying) or by making use of an oven, in particular at a temperature of 50° C.

The method of preparation according to the invention may be repeated several times in order to obtain a satisfactory degree of purity of the polysaccharide.

In an equally preferable manner, the method for preparing a composition according to the invention comprising a sulphated polysaccharide derived from a microalga includes:
 the culturing of the microalga, preferably in a photobioreactor;
 the concentration of the culture medium, after extraction of the biomass, in vacuo and at a temperature ranging from 30° C. to 50° C.;
 the extraction of the sulphated polysaccharide by diafiltration, precipitation or dialysis;
 the drying of the sulphated polysaccharide.

In an advantageous manner, the concentration of the medium is carried out at a temperature of 40° C.

Also in an advantageous manner, the extraction by precipitation may be carried out by centrifugation.

Also in an advantageous manner, the drying may be brought about by lyophilisation (freeze drying) or by making use of an oven, in particular at a temperature of 50° C.

The method of preparation according to the invention may be repeated several times in order to obtain a satisfactory degree of purity of the polysaccharide.

In an equally preferable manner, the method for preparing a composition according to the invention operationally implements a sulphated polysaccharide obtained by chemical modification of a polysaccharide.

This sulphated polysaccharide may be prepared by a method including a step of sulphation. The sulphation step may be carried out by various different methods that are known as such. This sulphation may in particular be brought about by making use of a $SO_3$/pyridine or $SO_3$/DMF (dimethylformamide) complex.

The objective of this sulphation step is to provide the polysaccharide with a rate of sulphation that is sufficient for the use of the composition according to the invention or indeed this objective is aimed at increasing the rate of sulphation of the polysaccharide.

The invention also relates to the use of a composition according to the invention as well as a composition according to the invention for use thereof:
 as an antiparasitic agent in humans or animals;
 in the treatment or prevention of an infection caused by at least one microsporidium in humans or animals;
 in the treatment or prevention of an infection in the honey bee caused by the microsporidium *Nosema*, preferably *Nosema ceranae* or *Nosema apis*;
 for stimulating the immune defence system of the honey bee.

The invention also relates to the use of a composition according to the invention as well as a composition according to the invention for use thereof in the production of honey, in the presence of an infection caused by at least one parasite, and comprising the administration to the honey bees of a composition according to the invention.

The invention also relates to the use of a composition according to the invention as well as a composition according to the invention for use thereof for maintaining the pollination of plants by honey bees that have been infected by at least one parasite, and comprising the administration to the honey bees of a composition according to the invention.

The invention also relates to a composition according to the invention for use thereof, on a prior-, simultaneous-, supplementary-, sequenced-, alternating-, or subsequent basis with respect to a treatment for fighting against *Varroa destructor*.

*Varroa destructor* is a hematophagous (blood sucking) mite, a parasite found in adult honey bees, larvae and pupae.

Thus, the use of a composition comprising at least one sulphated polysaccharide and at least one food ingredient is likely to maintain over time, indeed possibly even enhance the effectiveness of a treatment for fighting against *Varroa destructor*.

The composition used according to the invention is defined on the basis of the set of general, advantageous or preferred characteristic features of the composition according to the invention.

The invention also provides a kit comprising:
a composition according to the invention;
an agent to be used for controlling or preventing *Varroa destructor*, as well as such a kit for use thereof in the prevention or treatment of infections caused by the microsporidium *Nosema* and *Varroa destructor* in the honey bee.

The invention also relates to a sulphated polysaccharide defined for the composition according to the invention, for use thereof:
as an antiparasitic agent in humans or animals;
in the treatment or prevention of an infection caused by at least one microsporidium in humans or animals;
in the treatment or prevention of an infection in the honey bee caused by the microsporidium *Nosema*, preferably *Nosema ceranae* or *Nosema apis*;
for stimulating the immune defence system of the honey bee.

The invention also relates to a sulphated polysaccharide defined for the composition according to the invention for use thereof, on a prior-, simultaneous-, supplementary-, sequenced-, alternating-, or subsequent basis, with respect to a treatment for controlling *Varroa destructor*.

The polysaccharide according to the invention is defined on the basis of the set of general, advantageous or preferred characteristic features of the composition according to the invention.

The examples that follow are given by way of illustration of various different aspects of the invention.

Preparation of the Sulphated Polysaccharides

Sulphated Polysaccharide 1 (SP1):Iota Carrageenan

The extraction was based on a hot (60° C. to 90° C.) alkaline extraction (0.1 to 1M NaOH) over several hours, of a mixture of red marine algae belonging to the genera *Eucheuma, Kappaphycus, Chondrus* and *Betaphycus*. The resulting suspension obtained was filtered in order to remove the cell debris, and precipitated by addition of isopropanol. The precipitate was then pressed and dried.

The iota carrageenans include one repeating unit 3-β-D-galactopyranose and 4-α-D-galactopyranose alternating regularly. This latter unit is in anhydrogalactose form having significant rates of sulphation (30% to 50% on average). The average rate of sulphation is of the order of 30%

Sulphated Polysaccharide 2 (SP2)

The extraction was carried out after culturing a type of red microalgae *Rhodella violacea* (strain LMGE) on Hemerick medium or f/2.

The extraction of the biomass derived from this culture was carried out by centrifugation at 10,000 g×30 min at 10° C. The supernatant was then concentrated (2×) in vacuo at 60° C. and then dialysed for 72 hours against MilliQ water (9 baths) and then the retentate was dried by lyophilisation.

The monosaccharide composition of the SP2 thus obtained was determined by means of ion chromatography: xylose (20%), galactose (3%), glucose (0.5%), glucuronic acid (2.5%), arabinose (2%), rhamnose (3%). The percentages are percentages by weight.

Sulphated Polysaccharide 3 (SP3)

The extraction was carried out after culturing on f/2 medium of a type of red microalgae *Rhodella violacea* (Kornmann) Wehrmeyer CCAP 1388/5. The extraction of the biomass derived from this culture was carried out by centrifugation at 10,000 g×30 min at 10° C. The supernatant was then concentrated (2×) in vacuo at 60° C. and then dialysed for 72 hours against MilliQ water (9 baths) and then the retentate was dried by lyophilisation.

The monosaccharide composition of the SP3 thus obtained was determined by means of ion chromatography: xylose (20%), galactose (3%), glucose (0.5%), glucuronic acid (2.5%), arabinose (2%), rhamnose (3%). The percentages are percentages by weight.

Sulphated Polysaccharide 4 (SP4)

The extraction was carried out after culturing on f/2 medium of a type of microalgae *Rhodella maculata* CCAP 1388/2 (see Evans et al, *Studies on the synthesis and composition of extracellular mucilage in the unicellular red alga Rhodella*, Journal of Cell Science, 1974, 16, 1-21).

The extraction of the biomass derived from this culture was carried out by centrifugation at 10,000 g×30 min at 10° C. The supernatant was concentrated (2×) in vacuo at 60° C. and then dialysed for 72 hours against MilliQ water (9 baths) and then the retentate was dried by lyophilisation.

The exopolysaccharides of *Rhodella maculata* comprise carbohydrates (50%), proteins (16%), and a significant portion of sulphate (10%). The predominant monosaccharide is xylose. Uronic acids, galactose and glucose have also been identified.

Sulphated Polysaccharide 5 (SP5)

The extraction was carried out after culturing on f/2 medium of a type of microalgae *Porphyridium purpureum* (Bory) Drew & Ross (1965) CCAP 1380/1A.

The extraction of the biomass derived from this culture was carried out by centrifugation at 10,000 g×30 min at 10° C. The supernatant was then concentrated (2×) in vacuo at 60° C. and then dialysed for 72 hours against MilliQ water (9 baths) and then the retentate was dried by lyophilisation.

Sulphated Polysaccharide 6 (SP6)

The extraction was carried out after culturing on f/2 medium of a type of microalgae *Porphyridium marinum* Kylin (1937) CCAP 1380-1310.

The extraction of the biomass derived from this culture was carried out by centrifugation at 10,000 g×30 min at 10° C. The supernatant was concentrated (2×) in vacuo at 60° C. and then dialysed for 72 hours against MilliQ water (9 baths) and then the retentate was dried by lyophilisation.

Sulphated Polysaccharide 7 (SP7)

The extraction was carried out after culturing on Zarouk medium of a type of *cyanobacterium Arthrospira platensis* PCC8005. The extraction of the biomass derived from this culture was carried out by filtration on sintered glass having a porosity of 40 μm-100 μm (microns). The permeate was subsequently concentrated (2×) in vacuo at 60° C. and then dialysed for 72 hours against MilliQ water (9 baths) and then the retentate was dried by lyophilisation.

The exopolysaccharides from *Arthrospira platensis* are generally considered to be sulphated anionic heteropolysaccharides. The main monosaccharides that have been identified are galactose (14.9%), xylose (14.3%), glucose (13.2%), fructose (13.2%), rhamnose (3.7%), arabinose (1%), mannose (0.3%), and uronic acids (13.5% represented by galacturonic acid and glucuronic acid) (Trabelsi et al, *Partial characterization of extracellular polysaccharide produced by Artrospira platensis*. Biotechnology and Bioprocess Engineering, 2009, 14, 27-31).

Sulphated Polysaccharide 8 (SP8)

Dried algae of the type *Halymenia durvillei* were washed with water and then dried in an oven at 60° C.

The extraction of polysaccharides was subsequently carried out by heating under reflux in MilliQ water (1:20 ratio) for a period of 4 hours at 90° C. and then a filtration process on filtres of decreasing porosities (160 μm to 40 μm) was performed. The filtrate thus obtained was centrifuged at 10,000 g for a period of 30 min (ambient temperature). The supernatant was subsequently precipitated by addition of 3 volumes of 96% ethanol. The precipitate was subsequently collected by means of pressing or centrifugation (10,000 g for 20 min, ambient temperature) and then dried by lyophilisation.

The SP8 comprises 3-β-D-galactopyranose units and 4-α-D/L-galactopyranose units. The 3-β-D-galactopyranose unit is sulphated in position 2 (26%) and 2/6 (58%). The 4-α-D/L-galactopyranose unit is sulphated in position 6 (19%) and 2,6 (47%) and some residues are of the type 3,6 anhydrogalactopyranose.

The polysaccharide is connected by monosaccharides of such types as galactose, xylose, arabinose and fucose in minor amounts, and pyruvate was also detected (1.8%).

Sulphated Polysaccharide 9 (SP9)

The extraction was carried out on a type of dried microalgae *Ulva lactuca* that was depigmented by treatment with ethanol, acetone and chloroform. The extraction was carried out by incubation under reflux for a period of 3 hours at 90° C. in a solution of 50 mM sodium oxalate, pH6. After centrifugation at 12,000 g, for 30 min and at 4° C., the supernatant was precipitated with isopropanol, collected by centrifugation and then lyophilised.

The polysaccharide SP 9 is referred to by the term ulvan and is constituted of D-glucuronic acid, D-irduronic acid, D-xylose, L-rhamnose, and sulphate and is designated as a sulphated xylorhamnoglycuronan. Repeating units qualified as aldobiouronic acids have been identified (Ray et al, *Cell-wall polysaccharides from the marine green alga Ulva <<rigida>> (Ulvales chlorophytal) chemical structure of ulvan*. Carbohydrate Research, 1995, 274: 313-318).

EXAMPLE 1

Evaluation of Cytotoxicity of Sulphated Polysaccharides According to the Invention Culturing of HFF (Human Foreskin Fibroblast Cells in 96-Well Plate From a 75 cm² flask of HFF cells at confluence, the culture medium was removed, and then 2 mL of trypsin-EDTA (0.025% trypsin and 0.01% EDTA—Ethylenediaminetetraacetic acid) was added (at 37° C.). The flask was then briefly rinsed and the trypsin was removed. 2 mL of trypsin-EDTA was subsequently added and the flask was incubated for 5 minutes in an oven at 37° C.

5 ml of culture medium (minimal essential medium—MEM (PARA Laboratories GmbH)+Glutamine (2 mM)+Fungizone (2.5 μg/mL)+Penicillin (100 units/mL)+Streptomycin (100 μg/mL)+decomplemented Foetal Calf Serum 15%) was added and then the flask was rinsed with a pipette. The medium and cells were recovered in a tube. Counting on the Malassez counting chamber was then performed.

The cells were subsequently centrifuged at 200 g, for 7 minutes, and then the supernatant was removed. The pellet was taken up in the culture medium in a manner so as to obtain $10^5$ cells/mL.

200 μL of this suspension per well was distributed, while leaving empty the wells of columns 1 and 12 and rows A and H. The wells that were left empty were filled with 200 μL of culture medium in order to prevent evaporation.

Addition of Sulphated Polysaccharides

When the cells had reached confluence in the wells (about 48 hours), the medium was aspirated by making use of a vacuum extractor pump and then 200 μL of culture medium containing the various polysaccharides to be tested (the latter are tested at 50, 100, and 200 μg/mL) was added.

Each concentration was tested in triplicate. Each plate had to contain a negative control (culture medium without extract), a positive control (culture medium containing 20% of DMSO), and a fumagillin control (1 μg/mL). The results are summarised in Table 1 here below.

TABLE 1

|  | Viability (%) | Conclusion |
| --- | --- | --- |
| Healthy Cells Control | 100 +/− 2.3 | Control validated |
| DMSO Positive Control | 6.8 +/− 1.4 | Cytotoxic: control validated |
| Fumagillin Control | 99.1 +/− 12.2 | Non-cytotoxic: control validated |

Test of Cytotoxicity

After 96 hours of incubation, the medium contained in the wells was aspirated with a vacuum extractor pump and then 200 μL of fresh culture medium and 50 μL of TCA (Trichloroacetic acid) at 50% were added and the mixture was left for 5 minutes at ambient temperature and then for a period of 2 hours at 4° C.

The supernatant was removed with a vacuum extractor pump and washed 5 times (by overturning the 96-well plate) with 100 μL of distilled water and then the plate was dried (1 hour in the vacuum extractor pump, or 2 hours overturned on the bench). Once dried the plate was able to be stored at ambient temperature until subsequent use thereof.

100 μL of sulforhodamine B (0.4% in 1% acetic acid) was added and the mixture was incubated for 20 minutes at ambient temperature. The sulforhodamine B was removed by making use of a vacuum extractor pump. A wash cycle repeated 5 times (by overturning the 96-well plate) with 100 μL of 1% acetic acid was carried out and then the plate was dried for 5 minutes at ambient temperature by overturning it.

The proteins were solubilised by using 200 μL of Tris-Base (10 mM) for 5 minutes on a plate with stirring at ambient temperature. The OD (Optical Density) at 550 nm was measured by making use of a microplate reader (Multiskan FC357, Thermo Scientific).

The results are presented in Table 2 here below.

The mean of the OD and the standard deviation have been calculated for each sample tested in order to arrive at a conclusion with respect to the toxicity of the products.

TABLE 2

| | Viability (%) at 50 µg/mL | Viability (%) at 100 µg/mL | Viability (%) at 200 µg/mL | Conclusion |
|---|---|---|---|---|
| SP1 | 119.1 +/− 1.8 | 156 +/− 8 | 110 +/− 5 | Non-cytotoxic |
| SP2 | 95.6 +/− 13.7 | 89.2 +/− 6 | 69.2 +/− 7.8 | Non-cytotoxic up to 100 µg/mL |
| SP3 | 101.3 +/− 8.5 | 108.1 +/− 20.8 | 110 +/− 13.5 | Non-cytotoxic |
| SP4 | 94.2 +/− 5.2 | 98.7 +/− 20.8 | 97.3 +/− 8.8 | Non-cytotoxic |
| SP5 | 81.1 +/− 2.9 | 74.3 +/− 10 | 87.5 +/− 15.6 | Considered to be non-cytotoxic |
| SP6 | 84.4 +/− 13 | 89 +/− 6.4 | 63.7 +/− 5 | Non-cytotoxic up to 100 µg/mL |
| SP7 | 144.7 +/− 30.6 | 136.7 +/− 21.8 | 139.6 +/− 18.2 | Non-cytotoxic |
| SP8 | 143.7 +/− 35.7 | 142.2 +/− 31 | 96.7 +/− 22.3 | Non-cytotoxic |
| SP9 | 149.4 +/− 16.1 | 141.4 +/− 18.3 | 124.5 +/− 20.2 | Non-cytotoxic |

The results show that the sulphated polysaccharides according to the invention present no cytotoxicity, in particular up to 100 µg/mL.

EXAMPLE 2

Evaluation of the Anti-Parasitic Activity In Vitro on the Microsporidium Encephalitozoon *Cuniculi*, of Sulphated Polysaccharides According to the Invention Culturing of HFF (Human Foreskin Fibroblast) Cells in 48-Well Plates From a 75 cm² flask of HFF cells at confluence, the culture medium was removed, and then 2 mL of trypsin-EDTA (0.025% trypsin and 0.01% EDTA—Ethylenediaminetetraacetic acid) (at 37° C.) was added.

The flask was then briefly rinsed, and then the trypsin was removed. 2 mL of trypsin-EDTA (0.025% trypsin and 0.01% EDTA) was subsequently added and the plate was incubated for 5 minutes in an oven at 37° C.

5 ml of culture medium (MEM (PARA Laboratories GmbH)+Glutamine (2 mM)+Fungizone (2.5 µg/ml)+Penicillin (100 units/mL)+Streptomycin (100 µg/mL)+de-complemented Foetal Calf Serum 15%) were added and the dish was rinsed using the pipette. The medium and cells were recovered in a tube. Counting on the Malassez counting chamber was then performed. The cells were subsequently centrifuged at 200 g, for 7 minutes. The supernatant was then removed and the pellet was taken up in the culture medium in a manner so as to obtain $10^5$ cells/mL.

400 µL of this suspension per well was distributed, while leaving empty the wells of columns 1 and 8 and rows A and F. The wells that were left empty were filled with 400 µL of culture medium in order to prevent evaporation.

ELISA Test on Microsporidia

When the cells had reached confluence in the wells (about 48 hours), the medium was aspirated by making use of a vacuum extractor pump. Then 400 µL of culture medium containing the various polysaccharides to be tested (the latter were tested at the highest non-cytotoxic concentration, that is to say 100 or 200 µg/mL) was added, and then incubated for 2 hours in an oven at 37° C.

In parallel, a solution of spores of *Encephalitozoon cuniculi* (obtained from culture supernatant maintained in the laboratory) at a concentration of $5.10^5$ spores/mL was pre-incubated for 2 hours at 37° C. in the culture medium containing the polysaccharides to be tested. The spores were also pre-incubated under the same conditions but without polysaccharide, the said spores having served to infect the cells used to produce the negative control cited farther below. The latter was subsequently brought into contact for 1 hour at 37° C. with the cells, the polysaccharide being still present.

After a wash with PBS (Phosphate Buffered Saline) in order to remove the non-adherent spores, the various polysaccharides were added and thus left for the time period of the test operation (5 days). Each polysaccharide was tested in triplicate. Each plate contained an uninfected "healthy cells" control, a negative control (infected cells with no treatment) and a positive control (infected cells incubated in the presence of fumagillin at 1 µg/mL).

At the end of the test operation, the culture medium of each well was removed and a wash cycle with 200 µL of PBS was carried out. The wells were fixed individually with 100 µL of methanol for 20 minutes at −80° C. and then the cells were saturated with 100 µL of a blocking solution (100 mM Tris, 2% Bovine Serum Albumin BSA) for an entire night at 4° C.

The blocking solution was subsequently removed by making use of a vacuum extractor pump, then 100 µL of naturally infected rabbit serum (primary antibody) diluted to $\frac{1}{1,000}^{th}$ in the dilution buffer for antibodies (10 mM Tris pH=7.4, 150 mM NaCl, 0.05% Tween 20, 0.2% BSA) was added. The mixture was incubated for a period of 2 hours at 37° C. Then a wash cycle repeated 5 times with 200 µL of the washing solution (0.05% Tween 20, 10 mM Tris pH=9.8) was carried out. 100 µL of the anti-rabbit IgG secondary antibody (IgG Alkaline Phosphatase AP-conjugate Promega 1 mg/mL) coupled with alkaline phosphatase diluted to $\frac{1}{10,000}^{th}$ in the dilution buffer for antibodies was added. The mixture was incubated for a period of 1 hour at 37° C., and then a wash cycle repeated 5 times with 200 µL of the washing solution was carried out.

200 µL of 10 mM MUP (4-methylumbelliferyl phosphate) diluted to $\frac{1}{100}^{th}$ in the revelation solution (1 mM MgCl₂, 50 mM Na₂CO₃ pH=9.8) was added, and then the mixture was incubated for 30 minutes in the dark, under gentle agitation conditions.

The reading was carried out with fluoroscan with an excitation wavelength and an emission wavelength of 355 nm and 460 nm, respectively.

The results are presented in Table 3 here below.

The parasite growth inhibition data were calculated by taking into consideration the following information: the "healthy cells" control corresponds to the blank sample, the negative control (infected cells with no treatment) corresponds to 100% of parasite growth.

The inhibition capacity of the polysaccharides tested was evaluated on the basis of the following scale:
 <30%: low inhibition;
 between 30% and 40%: average inhibition;
 between 40% and 50%, satisfactory inhibition;
 between 50% and 70%: strong inhibition;
 between 70% and 90%: very strong inhibition;
 >90%: excellent inhibition.

TABLE 3

| Product | Inhibition of parasite growth/development (%) | Conclusion |
|---|---|---|
| SP1 (200 µg/mL) | 34.5 +/− 5 | average inhibition |
| SP2 (100 µg/mL) | 34.1 +/− 11.9 | average inhibition |
| SP3 (200 µg/mL) | 46.8 +/− 8.7 | satisfactory inhibition |

TABLE 3-continued

| Product | Inhibition of parasite growth/development (%) | Conclusion |
| --- | --- | --- |
| SP4 (200 µg/mL) | 29.9 +/− 4 | average inhibition |
| SP5 (200 µg/mL) | 99.4 +/− 1.1 | excellent inhibition |
| SP6 (100 µg/mL) | 90.3 +/− 16.7 | excellent inhibition |
| SP7 (200 µg/mL) | 48.3 +/− 11.3 | satisfactory inhibition |
| SP8 (200 µg/mL) | 35.7 +/− 7.4 | average inhibition |
| SP9 (200 µg/mL) | 35.9 +/− 0.7 | average inhibition |

The results show that the sulphated polysaccharides according to the invention exhibit satisfactory antiparasitic activity on microsporidia. The sulphated polysaccharides derived from a microalga of the genus *Porphyridium* show excellent growth inhibitory activity.

EXAMPLE 3

Evaluation of the Inhibitory Activity In Vivo of Sulphated Polysaccharides According to the Invention on *Nosema* in Honey Bees The results presented here have been obtained from the summer honey bees.
Retrieval/Recovery of Emerging (Newborn) Honey Bees and Maintenance in Beekeeping Box (Super)

After recovering one brood chamber frame (or more as per the needs in honey bees) from the apiary by means of a glass frame holder, the latter was placed in an oven at 34° C. for a period of 24 to 48 hours in a manner so as to allow the honey bees to emerge from their cells. Then, the young honey bees were retrieved from the frame by making use of a pair of entomologist's forceps and placed in the beekeeping boxes (supers) on the basis of 50 honey bees/box. $\frac{1}{6}^{th}$ of a tube stick of PseudoQueen (Contech Enterprises, Canada) was added in each of the beekeeping boxes.
Feeding of the Honey Bees Each polysaccharide treatment was carried out in triplicate (three boxes/treatment). Each test operation contained a "healthy honey bees" control (honey bees not infected and not treated), an "infected honey bees" control (honey bees infected experimentally and not treated) and a fumagillin control; with these controls also being in triplicate.

The honey bees were fed for a period of 3 days prior to infection with the syrup alone ("healthy honey bees" control and "infected honey bees" control), with syrup supplemented with 1 mg/ml fumagillin (fumagillin control), or with syrup containing the various sulphated polysaccharides to be tested (at the highest non-cytotoxic concentration, that is to say 100 or 200 µg/mL). The syrup was constituted of 50% of saccharose, supplemented with 1% of proteins (Provita'Bee, Laboratoires Corylis, France).

The feeding of the honey bees was accomplished by means of 5 mL transparent plastic tubes drilled at the ends thereof in order to enable the honey bees to feed themselves.
Individual Infection of the Honey Bees by *Nosema ceranae*

The honey bees had been kept in fasting condition for 30 to 60 minutes prior to infection. During this time, a solution of *Nosema ceranae* spores was prepared by diluting the latter in the feeding syrup on the basis of 125,000 spores for 3 µL. Each bee was thus infected with 125,000 spores.

The honey bees were subsequently gassed with $CO_2$ (about 1 minute/box). When honey bees began to wake up, they were withdrawn by making use of a pair of entomologist's forceps. The honey bees were subsequently individually infected via the oral route, by making use of a pipette containing 3 µL of the prepared solution of spores (by ensuring that the honey bees drank the 3 µL solution in its entirety). The same test operation was carried out with the boxes of the "healthy honey bees" control while ensuring that only the feeding syrup alone was given. 45 honey bees per box were placed in the supers.

After the infection step, to each of the boxes the feeding tubes were added so as to correspond to the different conditions (only syrup for the "healthy honey bees" control and "infected honey bees" control, syrup supplemented with 1 µg/mL fumagillin for the fumagillin control, syrup containing the various sulphated polysaccharides). Honey bees were placed in the oven at 33° C. (humidity 60-70%), and fed continuously for a period of 20 days.
Monitoring of the Test Operation During the Post-Infection Phase Over the course of the post-Infection phase (a time period of 20 days), the dead honey bees were counted and removed on a daily basis from each of the boxes in order to track and monitor mortality. The feeding tubes were replaced every two days until the end of the test operation. It was possible to weigh the feeding tubes with a view to monitoring the consumption of the various different feed treatments by the honey bees.

At the end of 20 days, 30 live honey bees (10 honey bees/box) were sacrificed for each of the conditions tested, in order to carry out a count of the *Nosema ceranae* spores with the objective of assessing the parasite load in the honey bees. For this, the intestine and rectal ampulla of each of the honey bees were dissected and then ground in a Potter mill in 100 µL of PBS. After 3 washes, the counting was performed on Kovacs chambers.

The results are presented in Table 4 here below.

TABLE 4

| | Mortality at 20 days post-infection (%) | Change in parasite load |
| --- | --- | --- |
| "Infected Honey Bees" Control | 53.3 +/− 13.6 | None |
| Fumagillin Control | 25.9 +/− 16.7 | Decrease of 63.4% |
| SP1 (200 µg/mL) | 60 +/− 8 | Decrease of 26.4% |
| SP3 (200 µg/mL) | 41.5 +/− 19 | Decrease of 0.6% |
| SP5 (200 µg/mL) | 43.7 +/− 6.8 | Decrease of 20.4% |
| SP6 (100 µg/mL) | 35.6 +/− 10.2 | Decrease of 33.8% |
| SP1-SP5 Mixture (100 µg/mL each) | 54.8 +/− 26.5 | Decrease of 6.25% |

The results showed a significant decrease in mortality of the honey bees when they were fed with a composition comprising a sulphated polysaccharide according to the invention.

The sulphated polysaccharide SP6 derived from *Porphyridium marinum* in particular shows a significant decrease in mortality among the honey bees.

Thus, the sulphated polysaccharides according to the invention provide the ability to limit the development and growth of the parasite (illustrated by the decline in the spore count) and thereby to significantly reduce the mortality rate among honey bees infected with *nosema* disease.

The invention claimed is:
1. A method for treating or preventing an infection caused in honey bees by the microsporidium *Nosema*, comprising administering to honey bees in need thereof an effective amount of a sulphated polysaccharide selected from the group consisting of:
- a sulphated polysaccharide derived from a red alga;
- a sulphated polysaccharide derived from a green macroalga of the Chlorophyceae species that produces polysaccharides;
- a sulphated polysaccharide derived from a brown macroalga of the Pheophyceae group that produces sulphated fucans; and
- a mixture thereof.

2. A method for stimulating immune defence systems of honey bees, comprising administering to honey bees in need thereof an effective amount of a sulphated polysaccharide selected from the group consisting of:
- a sulphated polysaccharide derived from a red alga;
- a sulphated polysaccharide derived from a green macroalga of the Chlorophyceae species that produces polysaccharides;
- a sulphated polysaccharide derived from a brown macroalga of the Pheophyceae group that produces sulphated fucans; and a mixture thereof.

3. The method according to claim 1, wherein the sulphated polysaccharide is included in a composition further comprising at least one food ingredient.

4. The method according to claim 1, wherein the sulphated polysaccharide is included in a composition further comprising at least one food ingredient selected from a dietary protein agent, a sugar including saccharose, a sugar including sucrose, honey or mixtures thereof.

5. The method according to claim 1, wherein the sulphated polysaccharide is derived from a macroalga and obtained by a method comprising the following steps:
- preparing a solution of the sulphated polysaccharide from the macroalgae, by heating under reflux in water at a temperature ranging from 50° C. to 100° C.;
- precipitating the sulphated polysaccharide using a polar solvent or by dialysis; and
- drying the sulphated polysaccharide.

6. The method according to claim 1, wherein the sulphated polysaccharide is derived from a microalga and obtained by a method comprising:
- culturing the microalga;
- concentrating the culture medium,
- after extraction of the biomass, in vacuo and at a temperature ranging from 30° C. to 50° C.;
- extracting the sulphated polysaccharide by diafiltration, precipitation or dialysis; and
- drying the sulphated polysaccharide.

7. The method according to claim 1, wherein:
- the sulphated polysaccharide is obtained by chemical modification of a polysaccharide; or
- the sulphated polysaccharide is prepared by a method including a step of sulphation; or
- the sulphated polysaccharide has a rate of sulphation on a weight basis that is greater than or equal to 5%; or
- the sulphated polysaccharide is comprised in a composition wherein the mass concentration of sulphated polysaccharide ranges from 50 to 1,000 mg/mL; or
- the sulphated polysaccharide is comprised in a composition further comprising at least one food ingredient, and wherein the sulphated polysaccharide/food ingredient ratio by weight ranges from 0.0001 to 0.002; or
- the sulphated polysaccharide is comprised in a composition further comprising at least one food ingredient, and wherein the food ingredient is selected from the group consisting of saccharose, sucrose, fructose, glucose, maltose, honey, and mixtures thereof; or
- the sulphated polysaccharide is comprised in a composition at a concentration by weight ranging from 0.01% to 2%; or
- the sulphated polysaccharide is comprised in a composition further comprising at least one food ingredient at a concentration by weight ranging from 98% to 99.99%.

8. The method according to claim 1, wherein the sulphated polysaccharide is derived from:
- a red macroalga selected from the Rhodophyceae species that produce agar, carrageenans, porphyrans, furonans, or complex sulphated galactans; or
- a red microalga selected from *Porphyridium marinum*, *Porphyridium purpureum*, and the *Rhodella* species.

9. The method according to claim 1, wherein the microsporidium *Nosema* is at least one of *Nosema ceranae* or *Nosema apis*.

* * * * *